(12) United States Patent
Shah

(10) Patent No.: US 12,161,351 B2
(45) Date of Patent: Dec. 10, 2024

(54) JIG FOR GUIDING PLACEMENT OF GLENOID COMPONENT OF THE IMPLANT IN SHOULDER REPLACEMENT SURGERY

(71) Applicant: Manish Shah, Ahmedabad (IN)

(72) Inventor: Manish Shah, Ahmedabad (IN)

( * ) Notice: Subject to any disclaimer, the term of this patent is extended or adjusted under 35 U.S.C. 154(b) by 343 days.

(21) Appl. No.: 17/619,198

(22) PCT Filed: Dec. 10, 2019

(86) PCT No.: PCT/IN2019/050901
§ 371 (c)(1),
(2) Date: Dec. 14, 2021

(87) PCT Pub. No.: WO2020/255152
PCT Pub. Date: Dec. 24, 2020

(65) Prior Publication Data
US 2022/0296259 A1  Sep. 22, 2022

(30) Foreign Application Priority Data

Jun. 21, 2019 (IN) .............................. 201921024718

(51) Int. Cl.
*A61B 17/17* (2006.01)
*A61F 2/40* (2006.01)
*A61F 2/46* (2006.01)

(52) U.S. Cl.
CPC ........ *A61B 17/1778* (2016.11); *A61F 2/4081* (2013.01); *A61F 2/4612* (2013.01)

(58) Field of Classification Search
CPC .. A61B 17/1778; A61F 2/4081; A61F 2/4612; A61F 2002/4677; A61F 2002/4687
See application file for complete search history.

(56) References Cited

U.S. PATENT DOCUMENTS

| 9,741,263 B2 | 8/2017 | Iannotti et al. ........ G09B 23/28 |
| 2006/0074430 A1 | 4/2006 | Deffenbaugh et al. ......... 606/87 |

(Continued)

FOREIGN PATENT DOCUMENTS

| CN | 103153240 A | 6/2013 |
| CN | 104271068 A | 1/2015 |

(Continued)

OTHER PUBLICATIONS

International Search Report mailed Apr. 28, 2020, issued to corresponding International Application No. PCT/IN2019/050901.

(Continued)

*Primary Examiner* — Samuel S Hanna
(74) *Attorney, Agent, or Firm* — Stein IP, LLC

(57) ABSTRACT

The present invention provides a jig for shoulder replacement surgery. In particular the present invention provides a pre-assembled jig that facilitates and guides the placement of glenoid component of the implant in shoulder replacement surgery. The present jig (P) is pre-assembled to ensure precision alignment, placing and sizing of the glenoid component of the implant for shoulder replacement surgery based on the difference of cuts in millimeters instead of the usual version measurements in degrees. The present invention (P) guides the glenoid component of shoulder replacement in the precise position and thereby provides accuracy in placement of the component.

4 Claims, 10 Drawing Sheets

(56) References Cited

U.S. PATENT DOCUMENTS

| | | | |
|---|---|---|---|
| 2013/0096564 A1 | 4/2013 | Winslow et al. | 606/96 |
| 2014/0303738 A1 | 10/2014 | Deffenbaugh et al. | A61F 2/4081 |
| 2016/0089163 A1 | 3/2016 | Eash et al. | A61F 17/1739 |
| 2016/0310285 A1 | 10/2016 | Kovacs et al. | A61F 2/40 |
| 2018/0078267 A1 | 3/2018 | Eash et al. | A61B 17/1778 |
| 2019/0015118 A1 | 1/2019 | Neichel et al. | A61B 17/1778 |
| 2021/0204967 A1* | 7/2021 | Lefebvre | A61B 17/1778 |

FOREIGN PATENT DOCUMENTS

| | | |
|---|---|---|
| CN | 204121146 U | 1/2015 |
| CN | 108135707 A | 6/2018 |
| FR | 2979536 A1 | 3/2013 |
| KR | 10-2019-0045646 A | 5/2019 |

OTHER PUBLICATIONS

Canadian Office Action dated Feb. 6, 2023, issued by the Canadian Patent Office in corresponding application CA 3,143,137.
Eurasian Office Action dated Sep. 28, 2022, issued by the Eurasian Patent Office in corresponding application EA 202193335.
Written Opinion dated Dec. 12, 2023, issued by the Intellectual Property Office of Singapore in corresponding application SG 11202113486Q.
Indian Office Action dated Jun. 4, 2020, issued by the Intellectual Property of India in corresponding application IN 201921024718.
Chinese Office Action dated Dec. 27, 2023, issued by the China National Intellectual Property Administration in corresponding application CN 201980097724.3.

* cited by examiner

JIG FOR GUIDING PLACEMENT OF GLENOID COMPONENT OF THE IMPLANT IN SHOULDER REPLACEMENT SURGERY

CROSS-REFERENCE TO RELATED APPLICATIONS

This application is a national stage of International Application No. PCT/IN2019/050901, Dec. 10, 2019, which claims the benefit of Indian Application No. 201921024718, filed Jun. 21, 2019, in the Indian Patent Office, the disclosure of which is incorporated herein by reference.

FIELD OF INVENTION

The present invention provides a jig for shoulder replacement surgery. In particular the present invention provides a pre-assembled jig that facilitates and guides the placement of glenoid component of the implant in shoulder replacement surgery. Moreover the present invention provides a pre-assembled modular jig that guides the placement of glenoid component of the implant in shoulder replacement surgery on the scapula precisely in three dimensions in terms of version, inclination, vertical height and side-to-side placement of implant; aiding surgeon to work with acumen. The present invention guides the glenoid component of shoulder replacement in the precise position and thereby provides accuracy in placement of the component. Furthermore, the present invention substantially reduces the time taken for the surgery and also decreases the chances of infection with less blood loss and minimum bone loss.

BACKGROUND OF INVENTION

The shoulder joint is made up of two bones: scapula and humerus. Shoulder replacement surgery (arthroplasty) is usually necessary when the cartilage covering the two bones of the shoulder joint (viz., glenoid portion of the scapula and upper part of humerus) is worn of damaged to the extent that one's mobility is reduced and one experiences pain while using the shoulder every time. Replacing the damaged shoulder joint with an optimum and sized artificial implant in an optimum position and alignment can help reduce pain and increase mobility.

The shoulder joint is the third most commonly replaced joint in the body after the hip and knee joints according to Fisher E S et al. During the shoulder replacement surgery in medical science following terms are frequently being used:
Meaning of Terms:

Displacement: The distance that the component is placed in any of the three planes (axial plane, sagittal plane and coronal plane) described below. The specific terms used for direction of displacement are described below the definitions of the planes.

Axial Plane: Axial plane referred herein after means; any plane that divides the body into superior (upper) and inferior (lower) parts, roughly perpendicular to spine.

Sagittal plane: Sagittal plane referred herein after means, any plane that divides the body into right and left parts or towards midline and away from the midline, roughly corresponding to the side view.

Coronal plane: Coronal plane referred herein after means: any plane that divides the body into front and back parts, roughly corresponding to front or back view.

Superior: Superior (from Latin) referred herein after means; above.

Inferior: Inferior (from Latin) referred herein after means; below.

Medial: Medial referred herein after means; pertaining to the middle or towards the middle; nearer to the middle of the body.

Lateral: Lateral referred herein after means; pertaining to being away from the middle; further away from the center of the body.

Anterior: Anterior referred to herein after means; front or towards the front part of the body.

Posterior: Posterior referred to herein after means; back or towards the back part of the body.

Versions: The term versions referred herein after means; the rotation along said axial plane.

Ante version: Ante version referred herein after means; rotation towards anterior (front) side.

Retroversion: Retroversion referred hereinafter means; rotation towards back side.

Inclination: the term inclination referred herein after means; the rotation along said coronal plane Superior inclination: Superior inclination referred herein after means; Inclination towards the superior side (above).

Inferior inclination: Inferior inclination referred herein after means; inclination towards the inferior side (below)

Moreover, conventional techniques are used by the surgeons for the shoulder replacement surgery. However, said techniques are not accurate and also lacks in ease of operation for the surgeons.

One such conventional technique in existence, is the use of guiding instruments (jigs) relying upon the X-Rays in the Shoulder replacement surgery. The technique utilizes existing guiding instruments (jigs) based on two dimensional X-ray analysis of the body part in the shoulder replacement surgery. X-rays are used in shoulder replacement surgery as a standard measure to investigate and plan tools required for the shoulder surgery. It is based on the single "snapshot" of the body part of the patient taken as X-Ray that provides a two dimensional image of bone for the analysis.

However there are many disadvantages associated with use guiding instruments (jigs) based on observations from X-rays in shoulder replacement surgery. It fails to determine the deformities at certain parts of the bones or between the bones. X-rays further shows deformities in varying degrees of magnification. Thus, accurate measurement of the deformities in millimeters cannot be assured using X-rays. The X-rays are unable to render a three dimensional surface representation and hence, the standard conventional jigs for the glenoid of the scapula bone are placed directly on the glenoid face and approximation in terms of angles found in average population are made universally without the accuracy and precision as per the patients need. The angle or the variation in angle, other deformities are arbitrarily calculated and decided by the surgeon. Therefore even the minor error in calculation or decision of the surgeon leads to failure of the entire surgery without any precision or accuracy.

Another technique that overcomes the above said variability of X-rays, is the use of guiding instruments (jigs) based on computed tomography scan CT-scan or Magnetic Resonance Imaging MRI scan. The use and importance of the CT-scan for preoperative planning of correct retroversion in the shoulder implant surgery was reported by Ganapathi et al.

However, there are many disadvantages associated with use guiding instruments (jigs) based on observations from CT-scan or MRI scan. Even though CT scan or MRI scan is a three dimensional imaging technique, quite often the output of said technique is in form of two dimensional images as on X-ray plates, which leads to failure in accuracy and precision Conventional two dimensional (2D) CT scan has been found to be unreliable in measurements of glenoid version and inclination in the shoulder replacement surgery, as reported by Budge M D, Lewis G S, Schaefer E, Coquia S, Flemming D J, Armstrong A D. Comparison of standard two-dimensional and three-dimensional corrected glenoid version measurements. J Shoulder Elbow Surg 2011; 20:577-83. Wherein they reported a difference of more than 5° in glenoid version in almost 50% of 2D compared with 3D CT, despite a high interobserver and intraobserver reliability for both techniques. Furthermore Daggett et al reported a mean difference of 1° on glenoid inclination on reformatted 2D CT scans compared with 3D. B.S. Also conventional measurements of glenoid version and inclination disclosed in Werner et al suggest on reformatted 2D CT scans are less accurate compared with 3D measurements. Thereby the conventional techniques lack in providing the precision and accuracy in terms of version and inclination in the shoulder implant surgery Using the data from 3D CT scans or MRI, the surgeon at present, has two options to improve accuracy and get predictable results: 1. to use computer navigation or 2. To use the patient specific guiding instruments (jig) derived from said 3D CT scan or MRI data. Computer navigation needs extended exposure during surgery for attachment of the navigation devices. It is a costly instrumentation with a need for a large amount of disposables which add to the cost. The surgery becomes more time consuming. The extended time and exposure lead to higher blood loss and can increase chances of infection.

Furthermore the use of image derived guiding instruments based on CT scan or MRI data are patient specific and thus are not reusable jigs. This adds on the financial burden and also increases or causes delay in scheduling the surgery as a patient specific jig needs at least three weeks of time pre-operatively. Such techniques are based on the surgeon's decision or third party decision for the measurements, version and inclination and thus are vulnerable to higher chances of error in surgery; which sometimes may also call for post-operative measures or a repeat surgery. Thus, advances like computer navigation and patient specific jigs are costly and time consuming.

Prior Art and its Disadvantages

US patent U.S. Pat. No. 9,741,263 B2 discloses a method for assisting a user with surgical implementation of a pre-operative plan includes generating a physical native tissue model of a native patient tissue. The physical native tissue model includes at least one primary patient tissue area including a surface of interest, at least one secondary patient tissue area including no surfaces of interest, and a base surface for engaging a supporting structure. The physical native tissue model, as generated, includes at least one information feature providing clinically useful information to the user. The information feature is substantially separated from the surface of interest. An apparatus for assisting a user with surgical implementation of a preoperative plan is also provided.

However said system fails to provide a modular reusable jig to guide the placement of glenoid in the shoulder replacement surgery that accurately and precisely guides the placement of glenoid component in patient as per the requirement. The jig uses the negative impression of surface imprints of the glenoid. As the negative impression of the glenoid is used, it needs extensive exposure of the bone devoid of soft tissue coverage. This leads to larger exposure and blood loss. Also the said system is user specific and hence fails to provide a reusable jig. As it is a single use product and needs to be manufactured, it is expensive and time consuming process with a delay of at least three weeks from time of CT scan.

Another instrument or system in use for the shoulder replacement surgery is the Arthrex VIP System. Said system consists of patient specific instruments that facilitates pre-operative planning and intra operative placement of the glenoid guide pin used in preparing the glenoid for implantation of the glenoid implant in the total shoulder Arthroplasty or reverse total shoulder arthroplasty. Based on the patient CT scan data submitted by the surgeon Arthrex Uses 3D preoperative planning software, to create a glenoid implant placement surgical plan for that specific patient.

However said system is bulky and is cumbersome to use due to 5D calibrator used in the system. This blocks the visualization of the surgeon during the placement surgery thereby increasing the chances of the error in the calculation of the placement of the component. Furthermore the time taken for the preoperative measures for surgery using said instrument is substantially more (approximately 48 hours). The accuracy of any reusable modular system depends on how well instrument sits on the glenoid bone. With a bulky instrument which blocks visualization, it is difficult to confirm that all five legs are sitting on the bone. This compromises the accuracy of the system. A lighter system which allows visual confirmation of seating of the jig on the bone is necessary.

Disadvantages of Prior Art:

Existing technologies and/or jigs used for the shoulder replacement surgery suffers from all or at least any of the below mentioned disadvantages:

- The conventional system fails to provide a pre-assembled jig that facilitates and guides the placement of glenoid component of the implant in shoulder replacement surgery.
- The conventional jigs for the placement of glenoid of the scapula bone are placed directly on the glenoid face and approximation in terms of versions found in average population are made. Whereas the version is alternatively decided arbitrarily by the surgeon. The placement of glenoid based on such approximation or arbitrary values are thereby fails not accurate and does not provide patient satisfaction.
- In particular, Conventional system for the shoulder implant surgery fails to provide modular jig that guides the placement of glenoid component of the implant in shoulder replacement surgery on the scapula precisely in three dimensions in terms of version, inclination, vertical height and side to side placement of the implant.
- Further the existing jigs for guiding implant placement in a shoulder replacement surgery relaying only on X-rays; fails to detect the deformities in the bones or between them, which leads to inappropriate calculation for the placement of the implant, and hence cannot be relied upon.
- The existing technologies using CT or MRI scans in 2D mode lack accurate detection of the deformities in the bones which further leads to the complexity in the surgery and post-surgery. Often Deformities are found out after the shoulder is opened for surgery; which increases the time for operating and at times, might require second surgery to solve the post-operative issues in the shoulder deformity; adding to the complexity of the surgery, pain and inconvenience to the patient along with the additional cost of post-surgical treatments Conventional techniques fails to provide a jig that precisely and accurately guides the implant over scapula at the definite version and inclination of the patient in the shoulder replacement surgery Moreover the existing techniques are time consuming and are not reliable as they are not accurate.

They fail to provide preoperative modular jig for the placement of the glenoid component in the shoulder replacement surgery.

Computer navigation used in the shoulder replacement surgery substantially increases the exposure of the shoulder and time needed during surgery along with the increased blood loss during the surgery and increased chances of infection, causing it painful for the patient; and thereby are not patient compliant.

Furthermore the conventional jigs based on 3D CT or MRI are not surgeon friendly as many of them are bulky, non-modular, are not reusable and requires approximate or arbitrary values based on assumption of the surgeon for the implant and in addition are also not precise and accurate.

Most of them based on 3D CT or MRI scans are patient specific and hence are not reusable thereby adding to the cost.

The existing system for reusable, modular jig based on 3D CT or MRI scans is bulky and are complex to use such that it blocks the vision of the surgeon during the surgery which in turn leads to many operative complexity during the surgery along with the lack of the precision and accuracy in the placement of the guide.

None of the prior art provides substantially effective instrument (Jig) to guide the placement of the glenoid component in shoulder replacement surgery that is accurate, precise in placing the implant component and is user friendly, patient compliant and reusable. Thus there is an unmet need of the invention that obviates the aforesaid problems of the prior art.

OBJECTS OF THE INVENTION

Accordingly the object of the present invention is to provide a jig for shoulder replacement surgery. In an aspect the present invention provides a pre-assembled jig that facilitates and guides the placement of glenoid component of the implant in shoulder replacement surgery.

It is an object of the present invention to provide a pre-operative modular jig that facilitates and guides the placement of glenoid component of the implant in shoulder replacement surgery. In an aspect the present invention provides a jig that guides the placement of glenoid component of the implant in shoulder replacement surgery on the scapula precisely in three dimension in terms of version, inclination, vertical height and depth of implant and aids the surgeon to work with acumen.

In another object, the present invention provides a jig that precisely and accurately guides the implant over scapula at the definite version and inclination of the patient in the shoulder replacement surgery.

In yet another object the present invention provides a modular jig that accurately determines the deformities in the bones or between the bones and thereby facilitate and guides the precise placement of glenoid component of the implant in shoulder replacement surgery.

In yet another object the present invention provides a jig for guiding placement of glenoid component of the implant in shoulder replacement surgery that considerably decreases the shoulder dissection thereby facilitating the shoulder replacement surgery less time consuming.

In an object the present invention eliminates the need of the arbitrary calculation of the values for the implant by the surgeon and/or third party thereby provides precision and accuracy and also reduces the time taken for the surgery which in turn requires the shoulder to be kept open for substantially less time and thereby decreases the chances of infections.

In yet another object the present invention provides reusable jig for guiding placement of glenoid component of the implant in shoulder replacement surgery. In an aspect the present invention provides a jig that reduces the blood loss and bone loss in guiding the placement of glenoid component of implant in shoulder replacement surgery.

In an object the present invention provides a jig for guiding placement of glenoid component of the implant in shoulder replacement surgery that is surgeon friendly and is not bulky and is easy to operate and visualize the placement of the component during the surgery.

In another object the present invention provides an accurate and precise jig for guiding the glenoid component of the implant in shoulder replacement surgery.

In other object the present invention provides a jig for guiding the glenoid component of the implant in shoulder replacement surgery that facilitates the surgeon to work with acumen.

In another object the present invention provides a jig for guiding the glenoid component of the implant in shoulder replacement surgery that aids in the shoulder replacement surgery and provides enhanced patient compliance reducing the blood loss, bone loss, chances of infection and post-operative difficulties, pain.

Figure 1:
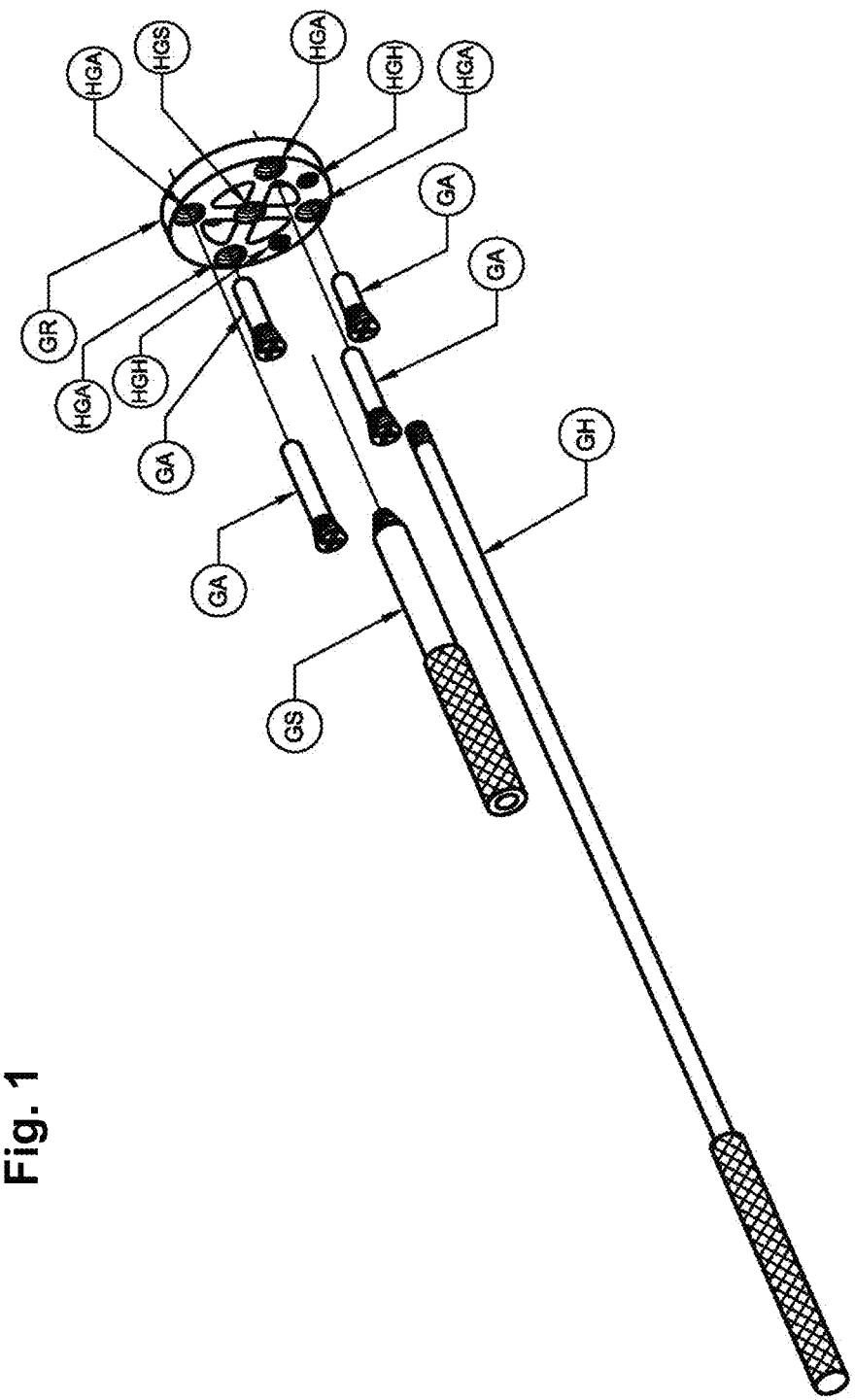
FIG. 1: | Shows the exploded view of the present jig for guiding the glenoid component of the implant in shoulder replacement surgery |
|

Meaning of Reference Numeral of the Said Component Parts of the Present Jig for Guiding the Glenoid Component of the Implant in Shoulder Replacement Surgery:
 P: Present jig for guiding the glenoid component of the implant in shoulder replacement surgery
 GR: Glenoid ring
 GS: Glenoid pin sleeve
 GA: Glenoid ring Augments
 GH: Glenoid ring handle
 HGA: Holes for Glenoid ring augments
 HGS: Hole for Guide pin sleeve
 HGH: Hole for Glenoid ring Handle
Additional References (not the Part of Present Jig)
 P1: Superior position of glenoid where the Glenoid ring Augment rests on the bone
 P2: Inferior position of glenoid where the Glenoid ring Augment rests on the bone
 P3: Anterior position of glenoid where the Glenoid ring Augment rests on the bone
 P4: Posterior position of glenoid where the Glenoid ring Augment rests on the bone

SUMMARY OF THE INVENTION

Referring to FIG. 1 to FIG. 7c, the present invention (P) comprises:
 Glenoid ring (GR),
 Glenoid pin sleeve (GS),
 Glenoid ring Augments (GA),
 Glenoid ring handle (GH),
 Holes for Glenoid ring augments (HGA),
 Hole for Glenoid pin sleeve (HGS),
 Hole for Glenoid ring Handle (HGH);

The present jig (P) uses measurements of displacement of Jig (P) of glenoid of the scapula bone, in a shoulder replacement surgery, wherein, to achieve precise cut as per the values of depth of cuts obtained from a system derived from 3D imaging like CT scans or MRI scans for obtaining accurate and precise position of the glenoid component of the shoulder replacement implant so as to achieve minimum bone loss and maximum patient satisfaction. While using the obtained values, the present Jig (P) is used to obtain precise cuts on the glenoid in a shoulder replacement surgery. The precise cuts on the glenoid are obtained by the precise placement of present Jig (P) on the scapula in all three planes to enable precise cuts on the bone. Wherein the precise placement is ensured by the precisely measured (more preferably in millimeters) glenoid ring augments (GA) that are used to generate rotations in different planes Placing of the present jig (P) on the scapula, establishes the contact of the present jig (P) with the bone at different points, such that the end of the glenoid ring augments (GA) touches the bone. Said points are termed herein after as contact points. Said contact points are used as reference points that enables the precise measurements while adjusting the Jig (P) to precise position and thereby facilitates in precise cuts. Wherein the contact points are in plurality more preferably three, four or more than three to achieve the precise adjustments of measurement.

Present description embodies four such contact points while achieving precise position and alignment of the present Jig (P) on the glenoid.
 P1: Base of glenoid ring augment (GA) in the Superior position of glenoid ring (GR) with cross hairs
 P2: Base of glenoid ring augment (GA) in the Inferior position of glenoid ring (GR) with cross hairs
 P3: Base of glenoid ring augment (GA) in the Anterior position of glenoid ring (GR) with cross hairs
 P4: Base of glenoid ring augment (GA) in the Posterior position of glenoid ring (GR) with cross hairs These four points controls the rotations and displacements of the present Jig (P) as under:
 Rotation in the sagittal plane: Superior inclination (inclination towards the superior side (above)) is controlled by increasing the size of the glenoid ring augment (GA) in inferior position of the glenoid ring (GR) with cross hairs over the glenoid augment (GA) in superior position of the glenoid ring (GR) with cross hairs (increasing the distance between P2 and ring compared to the distance between P1 and the ring). Similarly, inferior inclination (inclination towards the inferior side (below)) is controlled by increasing the size of the glenoid ring augment (GA) in superior position of the glenoid ring (GR) with cross hairs over the glenoid ring augment (GA) in inferior position of the glenoid ring (GR) with cross hairs (increasing the distance between P1 and ring compared to the distance between P2 and the ring) in the glenoid ring with cross hairs.

Rotation in axial plane: Anteversion (Rotation towards the front) is controlled by increasing the size of the glenoid ring augment (GA) in the posterior position of the glenoid ring (GR) with cross hairs over the glenoid ring augment (GA) in the anterior position of the glenoid ring (GR) with cross hairs (increasing the distance between P4 and ring compared to the distance between P3 and the ring) in the glenoid ring (GR) with cross hairs. Similarly, retroversion (Rotation towards the back) is controlled by increasing the size of the glenoid ring augment (GA) in the anterior position of the glenoid ring (GR) with cross hairs over the glenoid ring augment (GA) in the posterior position of the glenoid ring (GR) with cross hairs (increasing the distance between P4 and ring compared to the distance between P3 and the ring) with cross hairs.

Displacement in the sagittal plane is anterior or posterior placement. Displacement of P3 from anterior glenoid ring (GR) and P4 from posterior glenoid ring (GR) induces anterior or posterior placement of glenoid by the distance in millimeters as calculated in pre-operative planning.

Displacement in the axial plane is superior or inferior placement. Displacement of the glenoid ring (GR) at P1 from the superior edge and P2 from the inferior edge induces superior-inferior placement of the glenoid away from the inferior edge or the superior edge of the glenoid bone by the distance in millimeters as calculated in pre-operative planning.

Thus, the present Jig (P) uses measurements in millimeters (mm) in all three planes and all six degrees of freedom instead of the generally used angles in degrees in an undefined plane. Wherein the six degrees of freedom of movement are three angulations and three displacements. Further the Two angulations are Version in axial plane and inclination in coronal plane are as described above. The Third angulation in sagittal plane is rotation of the glenosphere on its axis, which is of no consequence as the glenoid implant in reverse shoulder arthroplasty is a hemi-sphere. Further the Two displacements Anterior-posterior in sagittal plane, superior-inferior in axial plane are as described above. Whereas the Third displacement, depth of placement of glenoid is controlled by depth of reaming on the guide pin.

DESCRIPTION OF THE INVENTION

The objective and particular technicalities of the invention are exemplified in the embodiment shown in accompanying drawings and as described herein below:

The embodiment of the present invention provides a pre-assembled modular jig for guiding the placement of glenoid component in the shoulder replacement surgery (P). It provides a jig that guides the placement of glenoid component of the implant in shoulder replacement surgery on the scapula precisely in three dimensions in terms of version, inclination, vertical height and side-to-side placement of implant. The present jig (P) is pre-assembled to ensure precision alignment, placing and sizing of the glenoid component of the implant for shoulder replacement surgery based on the difference of cuts in millimeters instead of the usual version measurements in degrees. The present invention (P) guides the glenoid component of shoulder replacement in the precise position and thereby provides accuracy in placement of the component. Furthermore the present invention (P) substantially reduces the time taken for the surgery and also decreases the chances of infection with less blood loss and minimum bone loss.

Figure 2:
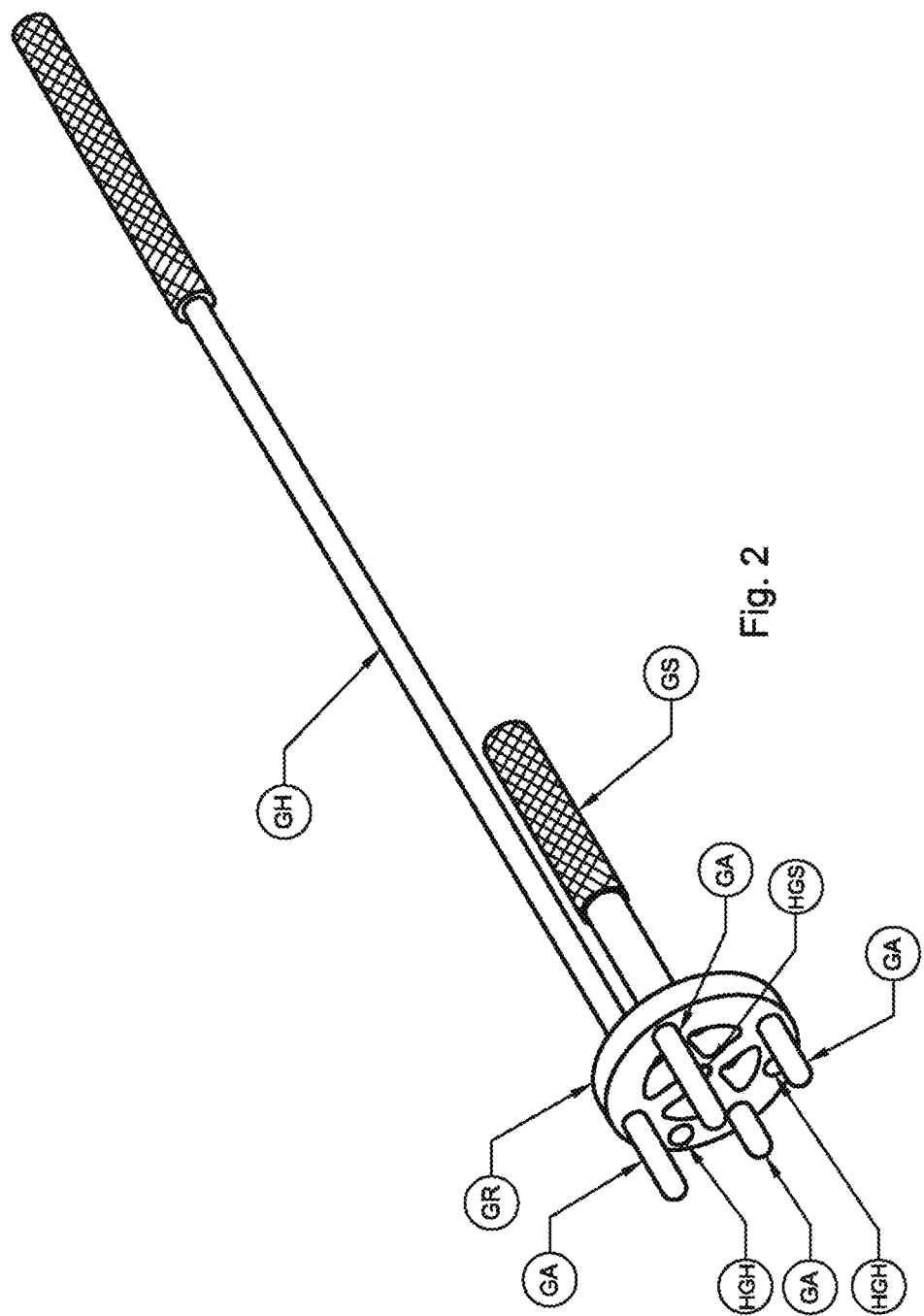
FIG. 2: | Shows the perspective view of present jig for guiding the glenoid component of the implant in shoulder replacement surgery |
|
Figure 3:
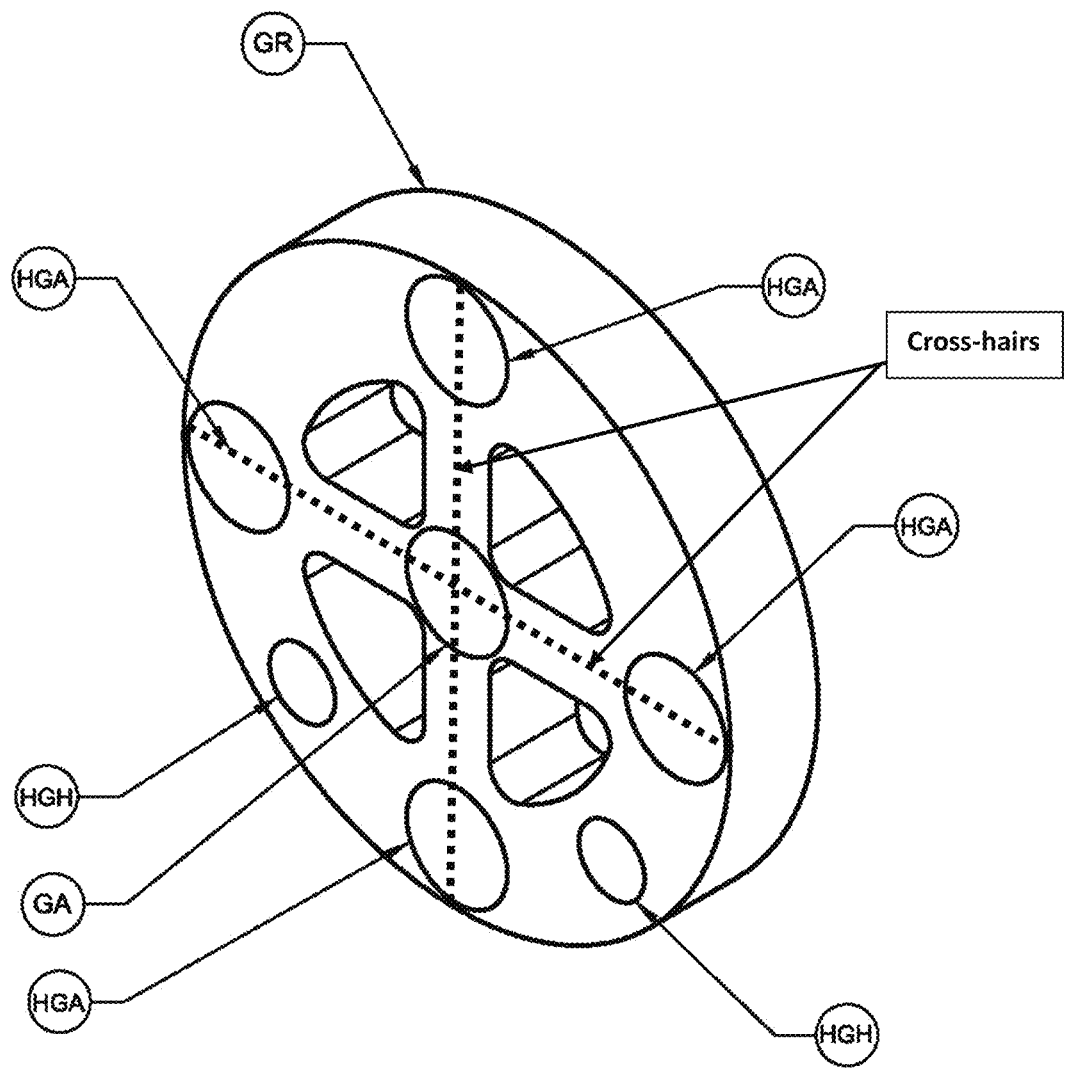
FIG. 3: | Shows the glenoid ring of the present jig for guiding the glenoid component of the implant in shoulder replacement surgery |
|

Referring to FIG. 1 and FIG. 2, the present jig for guiding the placement of glenoid component of the implant in shoulder replacement surgery (P) comprises:
Glenoid ring (GR).
Glenoid pin sleeve (GS),
Glenoid ring Augments (GA),
Glenoid ring handle (GH),
Holes for Glenoid ring augments (HGA),
Hole for Glenoid pin sleeve (HGS),
Hole for Glenoid ring Handle (HGH);
Wherein, Referring to FIG. 3 said glenoid ring (GR) has cross hairs and is preferably made of metal. Said glenoid ring (GR) facilitates holes for glenoid ring augments (HGA) at superior (P1), inferior (P2), anterior (P3) and posterior (P4) locations. Said holes for glenoid ring augments (HGA) are provided to accept said Glenoid ring augments (GA). Said glenoid ring (GR) further facilitates hole for glenoid ring handle (HGH) at anterior-inferior and postero-inferior end of the ring to accept the glenoid ring handle (GH). Alternatively the holes at anterior-inferior and postero-inferior end of the glenoid ring (GR) is used by the surgeon. Said Hole for glenoid pin sleeve (HGS) is provided at the center of the glenoid ring (GR) to accept the glenoid pin sleeve (GS). Said Glenoid Augments (GA) are provided such that it determines the four point of contacts on the shoulder of the patient undergoing the shoulder replacement surgery. The contact points where the glenoid ring augment (GA) rests on the bone are termed as P1 for superior glenoid ring augment, P2 for inferior glenoid ring augment. P3 for anterior glenoid ring augment and P4 for the posterior glenoid ring augment. Said glenoid augments (GA) are provided such that it facilitates in determining the position for the placement of glenoid component over scapula with accuracy and precision at the superior position (P1), Inferior position (P2), Anterior Position (P3), Posterior position (P4) of the glenoid.

Figure 4A:
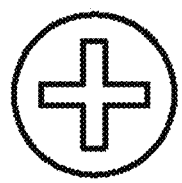
FIG. 4a and 4b: | Shows the variations in size measurements of the glenoid ring augments of the present jig for guiding the glenoid component of the implant in shoulder replacement surgery |
Figure 4B:
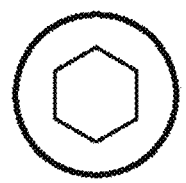
Figure 4C:
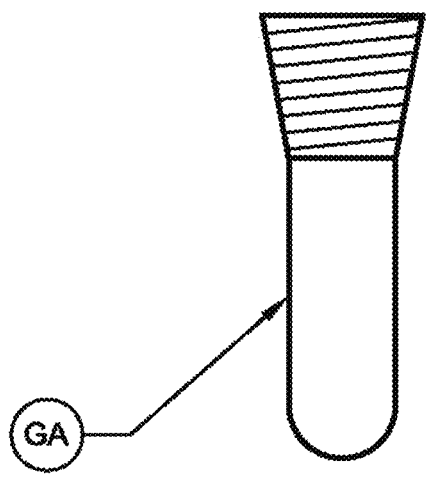
FIG. 4c and 4d: | Shows variations in head of the glenoid ring augments in top view of the present jig for guiding the glenoid component of the implant in shoulder replacement surgery |
|
Figure 4D:
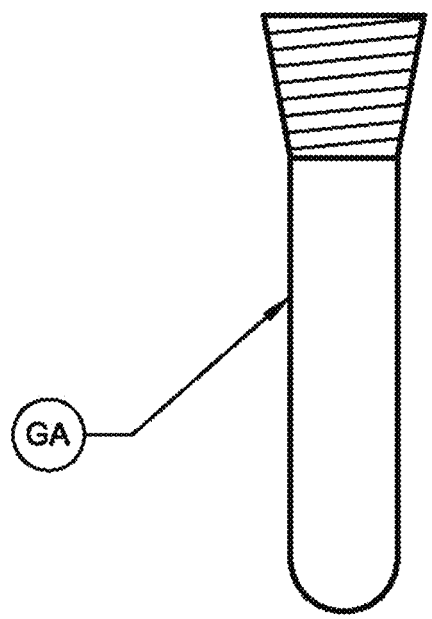

Now referring to FIG. 4c and FIG. 4d; shows the variation in the size measurements of said glenoid augments (GA). Wherein the size of glenoid augments (GA) varies in the range of 1 mm to 20 mm. Present Jig (P) determines the position for the accurate and precise placement of the glenoid component over scapula by controlling the lengths of said glenoid augments (GA) in four diametrically opposite directions. Further the rotations in the axial plane (versions) are also controlled by the lengths of the glenoid augments (GA) on the anterior position (P3) and posterior position (P4) of the glenoid ring (GR) with cross hairs. Where the anterior Glenoid ring augment (GA) is longer compared to posterior glenoid ring augment; that is the distance of glenoid ring augment (GA) from Anterior Position P3 is larger compared to the distance glenoid ring augment (GA) from Posterior position (P4). This increases retroversion. Where the posterior glenoid ring augment is longer compared to anterior glenoid ring augment increases the ante version. further said change in length of glenoid augments (GA) on superior position (P1) and Inferior Position (P2) of the glenoid ring (GR) with cross hairs rotating in coronal plane determines the inclination in terms of angle; where the superior position (P1) glenoid ring augment (GA) is longer compared to Inferior position (P2) glenoid augment (GA) indicates increase in inferior inclination angle over the scapula, where the superior position (P1) glenoid ring augment (GA) is shorter than Inferior position (P2) glenoid augment (GA) indicates increase in superior inclination angle over the scapula. The precise lengths of the glenoid ring augments (GA) are measured after studying the individualized CT scan by the surgeon and the distances of P3 and P4 from the glenoid ring are measured. For determining the inclination (the rotations in the coronal plane) the lengths of the glenoid augments (GA) on the superior position (P1) and Inferior Position (P2) of glenoid ring (GR) are changed. This determines the superior Inclination or inferior Inclination and accordingly the varied size measurements of the glenoid augments (GA) are used by the surgeon.

As shown in FIG. 4a and FIG. 4b the present jig (P), alternatively uses and discloses variations in the head of the glenoid augments (GA); more preferably a cross head on the top or hexagon head on the top of the glenoid augments (GA) of varied size ranges. The Glenoid ring augments (GA) are locked onto the ring with threads on the head of the glenoid ring augment (GA) and the threads in the holes of the glenoid ring with cross hairs (GR). Alternatively, different variations of locking mechanisms may be used to lock the glenoid ring augment into the holes in the glenoid ring with cross hairs for the glenoid ring augments.

Figure 6A:
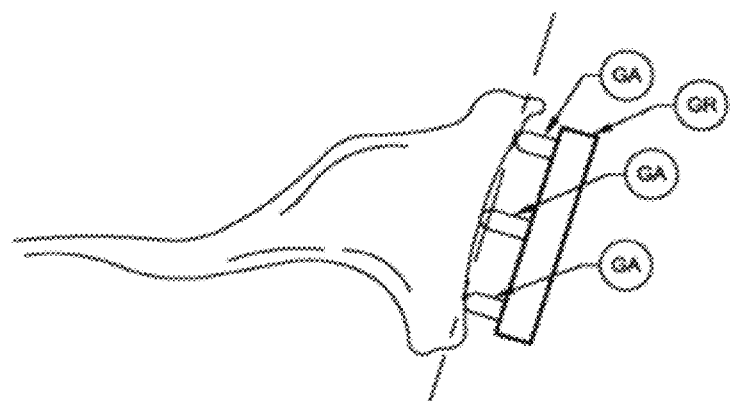
FIG. 6a: | Shows the increase in retro version with longer anterior glenoid ring augment on the scapula implementing the present jig for guiding the glenoid component of the implant in shoulder replacement surgery |
|
Figure 6B:
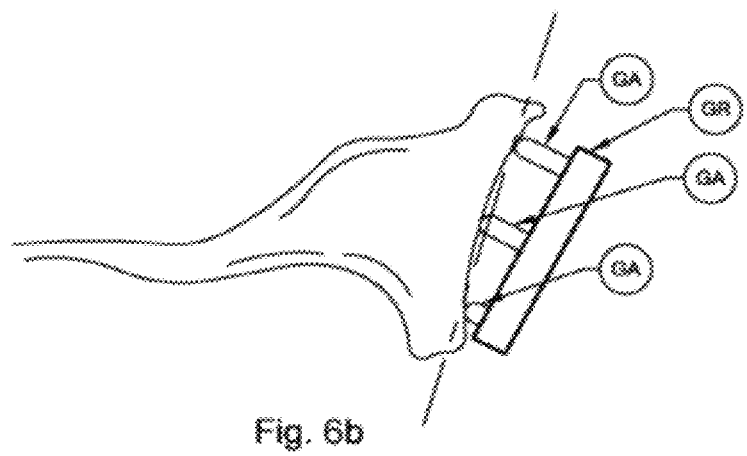
FIG. 6b: | Shows the increase in ante version with longer posterior glenoid ring augment on the scapula implementing the present jig for guiding the glenoid component of the implant in shoulder replacement surgery |
|
Figure 6C:
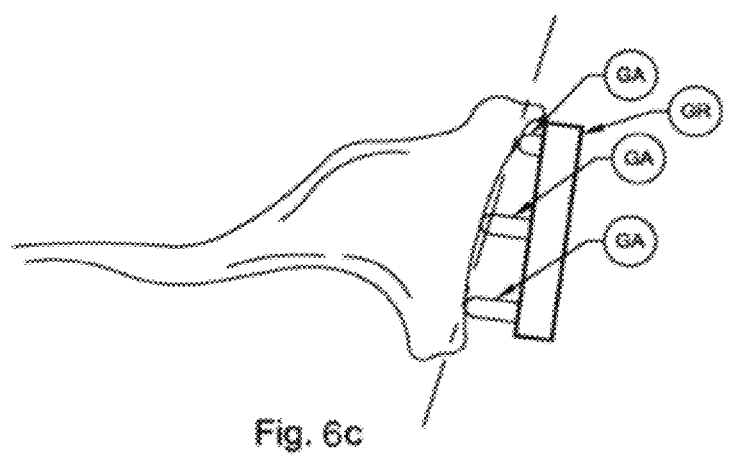
FIG. 6: | Shows the change in version with the change in augment size on the scapula implementing the present jig for guiding the glenoid component of the implant in shoulder replacement surgery. |
|

Referring to FIG. 6a to FIG. 6c, shows the changes in version with the change in the glenoid augment (GA) sizes on the scapula implementing the present jig for guiding the placement of glenoid component. The precise position of the placement of the component is ensured by the precisely measured sizes of glenoid augments (GA) as per the positions determined by the rotation and displacement in different planes. With the change in the size of the glenoid Augment (GA) as per the version precise variation in the angle is determined by the present jig (P) in three dimensions that are in the coronal, sagittal and axial planes. FIG. 6a shows the present jig (P) determining position over scapula of the patient for guiding the placement of the glenoid component at the reference points marking the points as Superior position of glenoid (P1), Inferior position of glenoid (P2), Anterior position of glenoid (P3), Posterior position of glenoid (P4). Based on the three dimensional report CT Scan/MRI of the patient and the pre-operative analysis the surgeon with the use of the present jig (P) determines the accurate and precise position for the glenoid placement. As shown in FIG. 6a, the surgeon implements various plurality of glenoid augments (GA) of varied size measurement according to the patient requirement. When the glenoid augment (GA) at the Anterior position of glenoid (P3) is longer than the glenoid augment (GA) at Posterior position of glenoid (P4); this generates the retro version over the scapula This precisely marks the position of the glenoid component over the scapula along with the variations in its inclination angle. Similarly, as shown in FIG. 6b, when the glenoid augment (GA) at the Anterior position of glenoid (P3) is shorter than the glenoid augment (GA) at Posterior position of glenoid (P4): this generates the ante version over the scapula. This precisely marks the position of the glenoid component over the scapula along with the variations in its version. Wherein the present invention (J) accurately detects the variations in versions (Retro and Ante) in terms of angle in the range of 1.8°-30°. Further said variations in the angle/s determined are directly proportional to the varied sizes of the glenoid augments (GA) in terms of millimeter (mm) in the range of 1 mm-20 mm being used in the present jig (P). Thus, with the change in the patient requirement, each glenoid augment (GA) is changed that accurately and precisely determines the version variations, that are specific to the patients and varies with each patient thereby aiding in the accurate placement of the glenoid component as per the patient need.

Figure 7A:
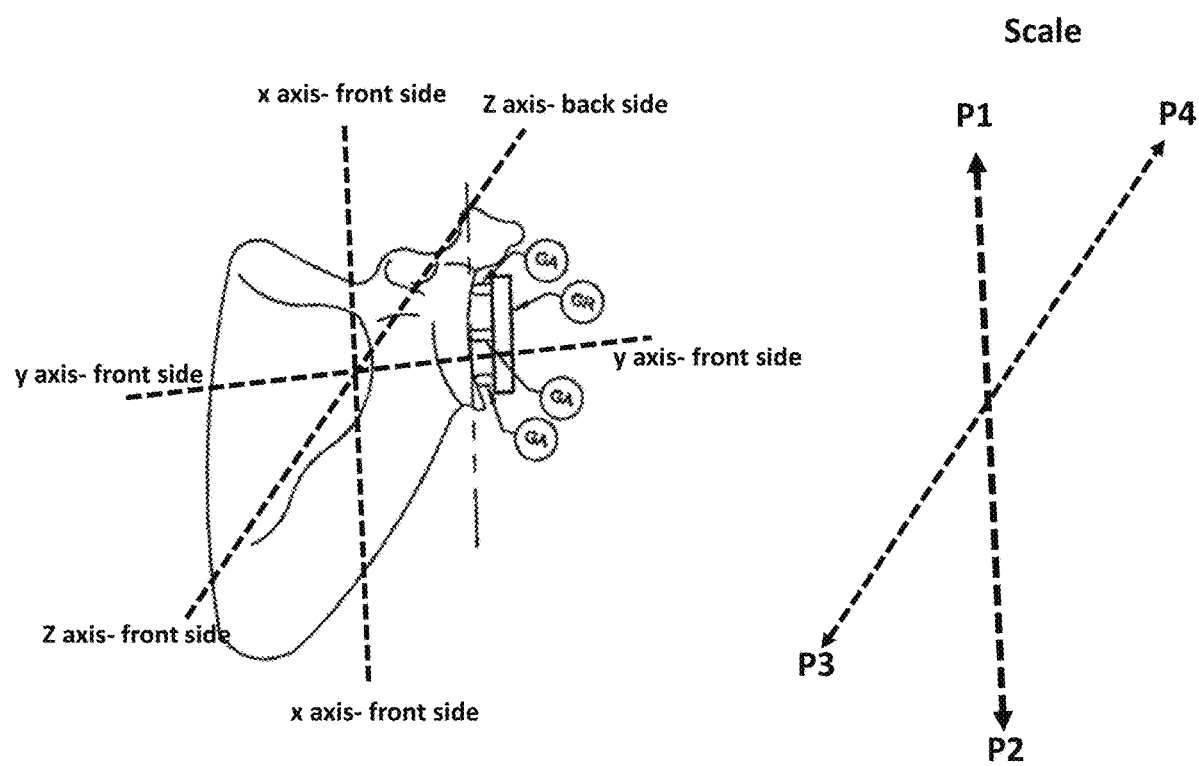
FIG. 7a: | Shows the increase in inclination with longer superior augment size on the scapula implementing the present jig for guiding the glenoid component of the implant in shoulder replacement surgery. |
|
Figure 7B:
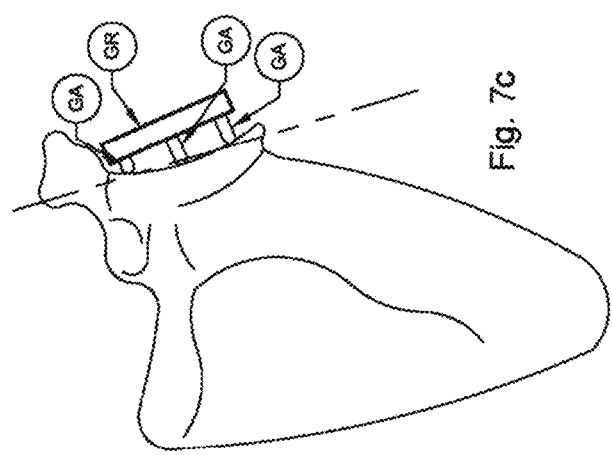
FIG. 7b: | Shows the decrease in inclination with longer inferior augment size on the scapula implementing the present jig for guiding the glenoid component of the implant in shoulder replacement surgery |
Figure 7C:
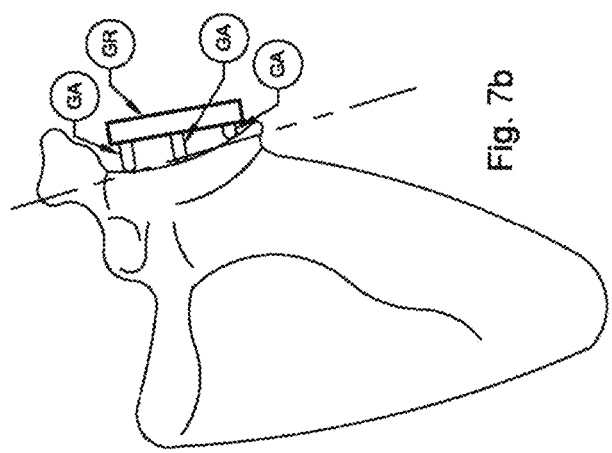
FIG. 7: | Shows the change in inclination with the change in augment size on the scapula implementing the present jig for guiding the glenoid component of the implant in shoulder replacement surgery |
|

FIG. 7a to FIG. 7c, show the change in inclination with the change in augment size on the scapula implementing the present jig (P). The precise position of the placement of the component is ensured by the precisely measured sizes of glenoid ring augments (GA) as per the positions determined by the rotation and displacement in different planes. With the change in the size of the glenoid ring Augment (GA) as per the inclination, precise variation in the angle is determined by the present jig (P) in three dimension. Referring to FIG. 7a, the present jig (P) determines position over scapula of the patient for guiding the placement of the glenoid component at the reference points marking the points as Superior position of glenoid (P1), and Inferior position of glenoid (P2). Anterior position of glenoid (P3), Posterior position of glenoid (P4). Based on the three dimensional report CT Scan/MRI of the patient and the pre-operative analysis the surgeon with the use of the present jig (P) determines the accurate and precise position for the glenoid placement (GA). As shown in FIG. 7c, the surgeon implements various plurality of glenoid augments (GA) of varied size measurement according to the patient requirement. When the glenoid augment (GA) at Superior position of glenoid (P1) is longer than the glenoid augment (GA) at Inferior position of glenoid (P2); determines the increase in the inferior inclination angle over the scapula. This precisely marks the position of the glenoid component over the scapula along with the variations in its inclination. Similarly, as shown in FIG. 7b when the glenoid augment (GA) at Superior position of glenoid (P1) is shorter than the glenoid augment (GA) at Inferior position of glenoid (P2): determines the increase in the superior inclination angle over the scapula. This precisely marks the position of the glenoid component over the scapula along with the variations in its inclination. Wherein the jig (J) accurately detects the variations in inclination (increased in superior or inferior inclination) in terms of angle in the range of 1.8°-30°. Further said variations in the angle/s determined are directly proportional to the varied sizes of the glenoid augments (GA) in terms of millimeter (mm) in the range of 1 mm-20 mm being used in the present jig (P). Thus with the change in the patient requirement, each glenoid augment (GA) is changed that accurately and precisely determines the inclination variations, that are specific to the patients and varies with each patient thereby aiding in the accurate placement of the glenoid component as per the patient need.

Figure 5A:
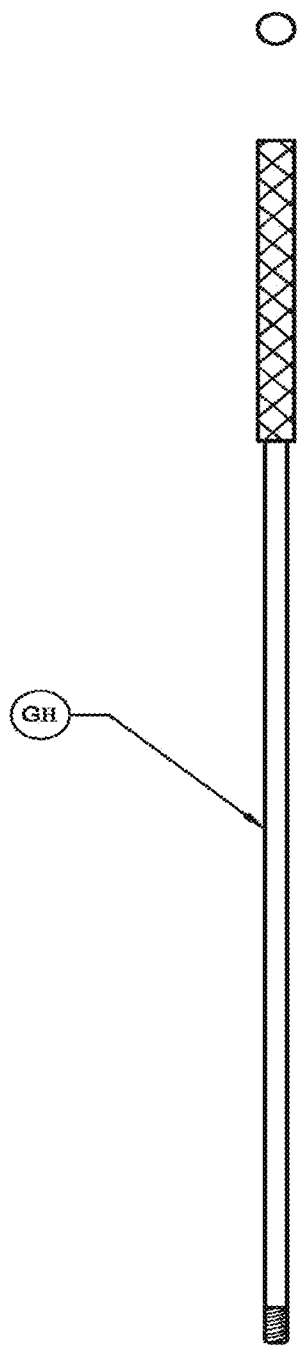
FIG. 5, 5a, 5b: | Shows the glenoid ring handle and its variations of the present jig for guiding the glenoid component of the implant in shoulder replacement surgery. |
|
Figure 5B:
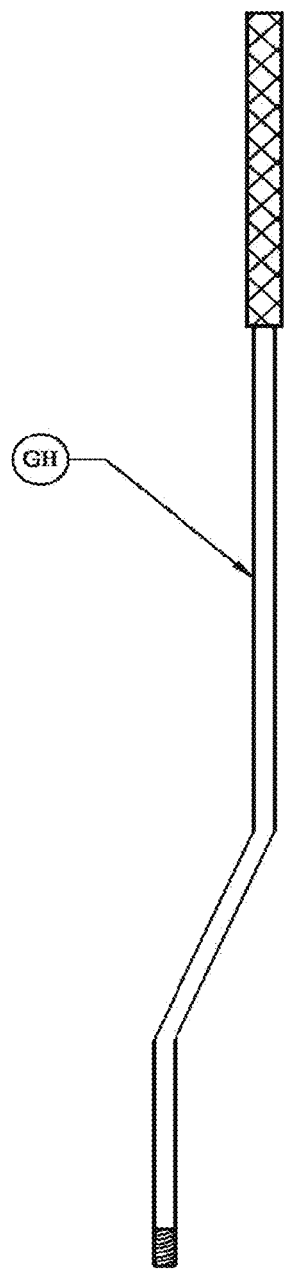
Figure 5C:
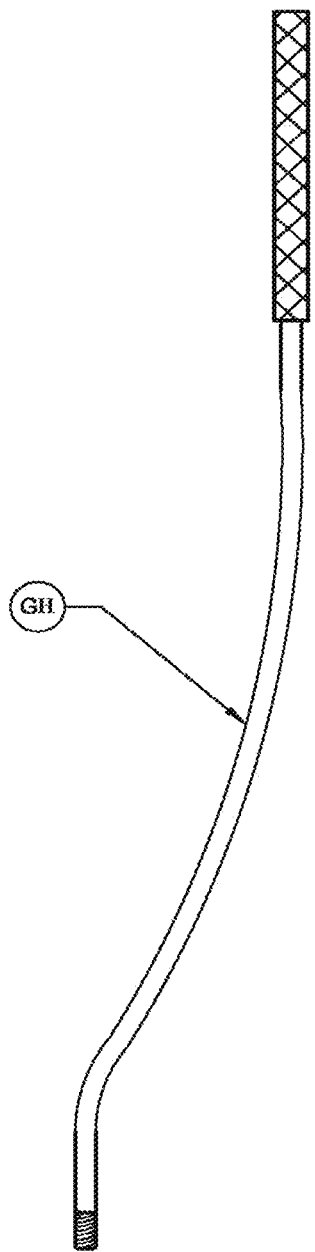

In an embodiment, the present invention (P), provides varied versions of the glenoid ring handle (GH) as shown in FIG. 5a to FIG. 5b. Said glenoid ring handle (GH) are provided to support the glenoid ring with cross hairs (GR) and are preferably made of metal with a grip at one end. On the other end a locking mechanism is provided that locks the glenoid ring handle (GH) into the hole for glenoid ring handle on the glenoid ring with cross hairs. Wherein said locking mechanism includes threads or its variations. The shape of the handle may vary as per surgeon preference for better visibility deep into the operative field without obstruction. Said glenoid pin sleeve (GS) is provided to facilitate precise direction for insertion of a guide pin (not shown in the Figures) and is preferably made up of metal with a grip at one end and locking mechanism at the other end. Wherein the other end of said glenoid pin sleeve (GS) is locked into the hole provided at the center of glenoid pin sleeve (HGS) in said glenoid ring with cross hairs (GR).

Working of the Invention:

The analysis for optimum fit implant and its optimum position is derived from any of the existing pre-operative system for the joint replacement surgery. The depth of cuts on the glenoid on the scapula along with the antero-posterior and superior-inferior distance is obtained from the said system. These are used to calculate the placement of the glenoid component and the size of the glenoid augments (GA) to be used. The working steps comprises of:
1. Determining contact points and verification of data obtained from pre-operative system
2. Assembling of the Present Jig (P),
3. Placement of the present jig (P) on the glenoid For the precise and the accurate placement of the glenoid component in the shoulder replacement surgery using the present Jig (P) the precise and accurate position for cut on the bone and the placement of the component with respect to version and inclination, said glenoid ring augments (GA) determines the four contact points namely superior (P1), inferior (P2), anterior (P3) and posterior (P4).

Determining Contact Points and Verification of Data Obtained from Pre-Operative System Following the determination the four contact points by the present jig (P), the surgeon verifies the data obtained from the preoperative system. This further ensures the accuracy of the operation of the present jig (P). The data obtained from the existing pre-operative system is verified by the surgeon as follows: In case where the surgeon feels to increase the "anteversion" as per the patient specific data obtained from the preoperative system; the surgeon uses the longer sized glenoid ring augment (GA) at the posterior position (P4) than the glenoid augment at the anterior position (P3).

In case where the surgeon feels to decrease the "anteversion" as per the patient specific data obtained from the preoperative system; the surgeon uses the longer sized glenoid ring augment (GA) at the anterior position (P3) than the glenoid augment at the posterior position (P4).

In case where the surgeon feels to increase the "inferior inclination" as per the patient specific data obtained from the preoperative system; the surgeon uses the longer sized glenoid ring augment (GA) at the superior position (P1) than the glenoid augment at the inferior position (P2).

In case where the surgeon feels to decrease the "inferior inclination" as per the patient specific data obtained from the preoperative system; the surgeon uses the longer sized glenoid ring augment (GA) at the inferior position (P2) than the glenoid augment at the superior position (P1).

Assembling of the Present Jig (P)

Further the glenoid augments (GA) as selected for use by the surgeon are locked into their respective holes for glenoid augments (HGA) starting with the superior hole. Wherein the difference in sizes of the glenoid augments (GA) used by the surgeon varies in the range of 1-20 mm with the corresponding degrees with the ratio of 1 mm:1.8° and 20 mm:30°.

Said guide pin sleeve (GS) is threaded and locked into the center of the hole for glenoid pin sleeve (HGS) in the glenoid ring with cross hairs (GR).

The glenoid ring handle (GH) is locked into the hole for glenoid ring handle (HGH) at either postero-inferior hole or antero-inferior hole depending on exposure of the glenoid and surgeon preference.

Placement of the Assembled Jig (P) Over Glenoid:
1. Said assembled jig is further placed on the glenoid surface taking care of the following:
    All four glenoid ring augments (GA) are touching the glenoid. This is crosschecked visually. Alternatively, an attempt can be made to pass small instrument under the glenoid ring augments (GA) to cross check that there is no space between the end of glenoid ring augment (GA) and the bone. the stability of the glenoid ring (GR) placed on the glenoid is assessed by a small toggle wherein, all four glenoid ring augments (GA) touches the glenoid surface, ensuring proper placement of glenoid ring (GR)
    Further the superior ring augment is aligned with the superior position of the glenoid
    The distance of placement of superior ring augment on glenoid (P1) from the superior position of the glenoid is the same as calculated from the pre-operative planning
    The distance of placement of inferior ring augment on glenoid (P2) from the inferior edge of the glenoid is the same as calculated from the pre-operative planning
    The distance of placement of anterior ring augment on glenoid (P3) from the anterior edge of the glenoid is the same as calculated from the pre-operative planning
    The distance of placement of posterior ring augment on glenoid (P4) from the posterior edge of the glenoid is the same as calculated from the pre-operative planning
2. Upon confirming the correct placement of the jig on the glenoid, the guide pin is drilled into the glenoid through the glenoid pin sleeve (GS) in the precise, desired angle and placement. A cannulated reamer (not shown in the Figures) is used over the guide pin to ream the glenoid and final preparations are made keeping the guide pin in place. The humerus is prepared and final components placed in either a cemented or uncemented mode. A spacer (not shown in the Figures) is placed and the wound is closed in layers.

Example 1

For patient A, based on CT-scan/MRI Reports and implying the results of the pre-operative system and doctors verification, the values calculated of Glenoid ring augments (GA) to be used for the Placement of Glenoid Component of the Implant in Shoulder Replacement Surgery were: For the glenoid ring Augment (GA) in superior position (P1) the value determined was 2 mm, for glenoid ring Augment (GA) in inferior position (P2) was 2 mm whereas for glenoid ring Augment (GA) in Anterior position (P3) was 3 mm and for glenoid ring Augment (GA) in the posterior position (P4) was 2 mm. Meaning thereby while applying the present invention for surgery in said patient the glenoid ring augments (GA) at the superior position (P1) and inferior position (P2) shall be same, since there is no change and variation detected in the inclination. Further for the said patient the glenoid ring augments (GA) at the Anterior position (P3) is larger than that at the posterior position (P4): thereby leading to retro version. There is the variation in version by 1 mm and 1.8° (in terms of degree). Hence the placement of the glenoid should be accordingly retroverted, where the glenoid ring augment (GA) used at the posterior position (P4) is larger by 1 mm than the glenoid ring augment (GA) at the anterior position (P3).

Example 2

For patient N, based on CT-scan/MRI Reports and implying the results of the pre-operative system and doctors verification, the values calculated of Glenoid ring augments (GA) to be used for the Placement of Glenoid Component of the Implant in Shoulder Replacement Surgery were: For the glenoid ring Augment (GA) in superior position (P1) the value determined was 2 mm, for glenoid ring Augment (GA) in inferior position (P2) was 2 mm whereas for glenoid ring Augment (GA) in Anterior position (P3) was 3 mm and for glenoid ring Augment (GA) in the posterior position (P4) was 4 mm. Meaning thereby while applying the present invention for surgery in said patient the glenoid ring augments (GA) at the superior position (P1) and inferior position (P2) shall be same, since there is no change and variation detected in the inclination. Further for the said patient the glenoid ring augments (GA) at the Anterior position (P3) is shorter than that at the posterior position (P4), thereby leading to ante version. There is the variation in version by 1 mm and 1.8° (in terms of degree). Hence the placement of the glenoid should be accordingly ante verted, where the glenoid ring augment (GA) used at the anterior position (P3) is larger by 1 mm than the glenoid ring augment (GA) at the posterior position (P4).

Example 3

For patient X, based on CT-scan/MRI Reports and implying the results of the pre-operative system and doctors verification, the values calculated of Glenoid ring augments (GA) to be used for the Placement of Glenoid Component of the Implant in Shoulder Replacement Surgery were: For the glenoid ring Augment (GA) in superior position (P1) the value determined was 4 mm, for glenoid ring Augment (GA) in inferior position (P2) was 2 mm whereas for glenoid ring Augment (GA) in Anterior position (P3) was 2 mm and for glenoid ring Augment (GA) in the posterior position (P4) was 2 mm. Meaning thereby while applying the present invention for surgery in said patient the glenoid ring augments (GA) at the superior position (P1) is larger than that at the inferior position (P2) leading to increase in inferior inclination. There is the variation in inferior inclination by 2 mm and 3.5° (in terms of degree) Hence the placement of the glenoid should be accordingly used, where the glenoid ring augment (GA) at the inferior position (P2) is larger by 2 mm than that used at the superior position (P1). Also, since the glenoid ring augments (GA) at anterior position (P3) and posterior position (P4) are same there is no change detected in version.

Example 4

For patient Y, based on CT-scan/MRI Reports and implying the results of the pre-operative system and doctors verification, the values calculated of Glenoid ring augments (GA) to be used for the Placement of Glenoid Component of the Implant in Shoulder Replacement Surgery were: For the glenoid ring Augment (GA) in superior position (P1) the value determined was 2 mm, for glenoid ring Augment (GA) in inferior position (P2) was 4 mm whereas for glenoid ring Augment (GA) in Anterior position (P3) was 2 mm and for glenoid ring Augment (GA) in the posterior position (P4) was 3 mm. Meaning thereby while applying the present invention for surgery in said patient the glenoid ring augments (GA) at the superior position (P1) is shorter than that at the inferior position (P2) leading to increase in superior inclination. There is the variation in superior inclination by 2 mm and 3.5° (in terms of degree). Hence the placement of the glenoid should be accordingly used, where the glenoid ring augment (GA) at the superior position (P1) is larger by 2 mm than that used at the inferior position (P2). Furthermore, the glenoid ring augment (GA) at anterior position (P3) is shorter than the glenoid ring augment (GA) at Posterior position (P4) leading to ante version. There is the variation in version by 1 mm and 1.8° (in terms of degree). Hence the placement of the glenoid should be accordingly ante verted, where the glenoid ring augment (GA) used at the anterior position (P3) is larger by 1 mm than the glenoid ring augment (GA) at the posterior position (P4).

Example 5

For patient B, based on CT-scan/MRI Reports and implying the results of the pre-operative system and doctors verification, the values calculated of Glenoid ring augments (GA) to be used for the Placement of Glenoid Component of the Implant in Shoulder Replacement Surgery were: For the glenoid ring Augment (GA) in superior position (P1) the value determined was 2 mm, for glenoid ring Augment (GA) in inferior position (P2) was 2 mm whereas for glenoid ring Augment (GA) in Anterior position (P3) was 3 mm and for glenoid ring Augment (GA) in the posterior position (P4) was 4 mm. Meaning thereby while applying the present invention for surgery in said patient the glenoid ring augments (GA) at the superior position (P1) and inferior position (P2) shall be same, since there is no change and variation detected in the inclination. Further for the said patient the glenoid ring augments (GA) at the Anterior position (P3) is shorter than that at the posterior position (P4), thereby leading to ante version. There is the variation in version by 1 mm and 1.8° (in terms of degree)). However here the glenoid of the patient was shallower and hence for the precise placement of the glenoid component, the glenoid augment (GA) at anterior position (P3) and at Posterior position (P4) had to be increased by 1 mm compared to glenoid augments at superior position (P1) and inferior position (P2).

Having described what is considered the best form presently contemplated for embodying the present invention, various alterations, modifications, and/or alternative applications of the invention for any system will be promptly apparent to those skilled in the art. Therefore, it is to be understood that the present invention is not limited to the practical aspects of the actual preferred embodiments hereby described and that any such modifications and variations must be considered as being within the spirit and the scope of the invention, as described in the above description.

The invention claimed is:

1. A pre-assembled jig for guiding a placement of a glenoid component in shoulder replacement surgery (P) in three dimensions in terms of version, inclination, vertical height and side-to-side placement of implant, the pre-assembled jig comprising:
    a glenoid ring (GR) with cross hairs;
    a glenoid pin sleeve (GS);
    glenoid ring augments (GA);
    a glenoid ring handle (GH);
    holes for glenoid ring augments (HGA);
    a hole for glenoid pin sleeve (HGS); and
    holes for glenoid ring handle (HGH);
    wherein
    said glenoid ring (GR) comprises:
        at least four of the holes for glenoid ring augments (HGA) at superior (P1), inferior (P2), anterior (P3) and posterior (P4) positions, respectively,
        the holes for glenoid ring handle (HGH) at anterior-inferior and posterior-inferior end, respectively, to accept the glenoid ring handle (GH), the hole for glenoid pin sleeve (HGS) at a center of the glenoid ring and configured to accept said glenoid pin sleeve (GS), said holes for glenoid ring augments (HGA) being configured to accept the glenoid ring augments (GA) of varied size measurements and with variations in types of heads of the glenoid ring augments (GA);

said glenoid ring augments (GA) configured to determine four points of contact on a shoulder of a patient;

said glenoid ring handle (GH) having a grip at one end and a locking mechanism at the other end for locking the glenoid ring handle into the hole for glenoid ring handle (HGH), said glenoid ring handle supporting the glenoid ring, said glenoid pin sleeve (GS) having a grip at one end and a locking mechanism at the other end locked into the hole for the glenoid pin sleeve (HGS), and configured to facilitate precise direction for insertion of a guide pin therethrough;

wherein lengths of said glenoid augments (GA) are different, differences in the lengths of the glenoid augments (GA) on the anterior position (P3) and the posterior position (P4) of the glenoid ring (GR) rotate the glenoid ring (GR) in an axial plane to adjust angle of the glenoid ring (GR) relative to a scapula;

where the anterior position (P3) glenoid ring augment (GA) is longer compared to the posterior position (P4) glenoid ring augment, indicating an increase in retroversion, and where the posterior position (P4) glenoid ring augment is longer compared to the anterior position (P3) glenoid ring augment, indicating an increase in an anteversion;

wherein differences in the length of the glenoid augments (GA) on the superior position (P1) and the inferior position (P2) of the glenoid ring (GR) rotate the glenoid ring (GR) in a coronal plane to determine inclination in terms of angle; where the superior position (P1) glenoid ring augment (GA) is longer compared to the inferior position (P2) glenoid augment (GA) indicating an increase in inferior inclination angle over the scapula; where the superior position (P1) glenoid ring augment (GA) is shorter than the inferior position (P2) glenoid augment (GA) indicating an increase in superior inclination angle over the scapula; and wherein the glenoid ring handle (GH) has end portions that are parallel, with a bent portion in between the ends of the glenoid ring handle (GH).

2. The pre-assembled jig as claimed in claim 1, wherein the variation in size measurements of said glenoid augments (GA) is in a range of 1 mm to 20 mm, and the variation in heads of glenoid Augments (GA) are cross head on the top or hexagon head on a top of the glenoid augments (GA).

3. The pre-assembled jig as claimed in claim 1, wherein a rotation in an axial plane and precise variation in version identified in terms of angles is in a range of 1.8°-30°, wherein said version variations in the angles determined are directly proportional to the varied sizes of the glenoid augments (GA) in terms of millimeter (mm) in a range of 1 mm-20 mm.

4. The pre-assembled jig as claimed in claim 1, wherein a rotation in a coronal plane and precise variation in inclination identified in terms of angles is in a range of 1.8°-30°, wherein said inclination variations in the angle determined are directly proportional to the varied sizes of the glenoid augments (GA) in terms of millimeter (mm) in a range of 1 mm-20 mm.

\* \* \* \* \*